United States Patent [19]
Kusunoki et al.

[11] Patent Number: 6,039,971
[45] Date of Patent: Mar. 21, 2000

[54] COMPOSITION FOR SKIN PATCH PREPARATION AND PROCESS FOR PREPARING THE SAME

[75] Inventors: Akihiko Kusunoki; Naohisa Kawamura; Yoshiki Sugizaki, all of Saitama-ken; Akio Kuwahara, Fukuoka-ken, all of Japan

[73] Assignee: Saitama Daiichi Pharmaceutical Co., Ltd., Kasukabe, Japan

[21] Appl. No.: 09/025,191

[22] Filed: Feb. 18, 1998

[30]     Foreign Application Priority Data

Mar. 24, 1997   [JP]   Japan ..................... 9-088735

[51] Int. Cl.⁷ ........................ A61K 9/70; A61L 5/60
[52] U.S. Cl. ........................... 424/443; 525/363
[58] Field of Search ............... 525/363; 424/443

[56]          References Cited

U.S. PATENT DOCUMENTS

| | | | |
|---|---|---|---|
| 3,839,255 | 10/1974 | Podlas | 524/320 |
| 5,116,621 | 5/1992 | Oji et al. | 424/445 |

FOREIGN PATENT DOCUMENTS

| | | |
|---|---|---|
| 61-41926 | 9/1986 | Japan . |
| 3-33685 | 5/1991 | Japan . |

OTHER PUBLICATIONS

Kusunoki et al, Physicochemical Reaction Characteristics of Patches Comprising Aluminum–Crosslinked Gel of Partially Neutralized Polyacrylic Acid, The Abstracts of the 117th Annual Meeting of Pharmaceutical Society of Japan, 27[G3] 15–1, Mar. 5, 1997 and English language translation.

*Primary Examiner*—Peter F. Kulkosky
*Attorney, Agent, or Firm*—Frishauf, Holtz, Goodman, Langer & Chick, P.C.

[57]            ABSTRACT

A composition for a skin patch including a synthetic polymer gel prepared by reacting a water-soluble polymer of an aliphatic carboxylic acid or a salt thereof with a sparingly soluble aluminum compound, an organic acid containing a hydroxyl group in its molecule as a reaction accelerator, and an ethylenediamine compound as a reaction inhibitor in the presence of water at a pH of 4.0 to 6.1. The composition can homogeneously gel at any crosslinking rate and does not cause any change in quality with the lapse of time.

15 Claims, 3 Drawing Sheets

COMPOSITION FOR SKIN PATCH PREPARATION AND PROCESS FOR PREPARING THE SAME

BACKGROUND OF THE INVENTION

1. Field of the Invention

The present invention relates to a composition of a skin patch preparation comprising a hydrophilic synthetic polymer gel, which can homogeneously gel at any desired crosslinking rate, has tack strength according to the purpose, does not change with the lapse of time, and a process for preparing the same.

2. Description of the Prior Art

The following physical properties have hitherto been required of a composition of a skin patch preparation.

(1) Tackiness: it can be well applied to the skin, can conform to the movement of the affected part, and enables this tackiness to persist for a long period of time.

(2) Insolubility: it can gel to a suitable extent and, even when perspiration occurs, becomes neither sticky nor softened.

(3) Peelability: it can be peeled without leaving any external preparation.

(4) Stability; it neither hardens nor becomes sticky upon a change in temperature or with the lapse of a long period of time.

(5) High water content: it can contain a large amount of water (the larger the water content, the better the effect of cooling the affected part).

A composition prepared merely by mixing aqueous solutions of several water-soluble polymer materials, such as gelatin, is among conventional compositions of a skin patch preparation. This composition cannot, of course, satisfy the above various characteristics. For example, an attempt has been made to react gelatin with glutaraldehyde or urea to insolubilize the composition. In this case, the crosslinking rate is excessively high, or otherwise the crosslinking occurs only under given conditions of temperature, pH and the like, making it difficult to prepare a composition of an external preparation having a satisfactory degree of crosslinking. Therefore, no composition of an external preparation which can satisfy the above various characteristics can be provided. A gel prepared by crosslinking a water-soluble polymer of an aliphatic carboxylic acid or a salt thereof with aluminum is known to have excellent characteristics. The incorporation, however, of a polyvalent metal ion in an amount exceeding a specified value under stirring into a viscous liquid containing a water-soluble polymer of an aliphatic carboxylic acid or a salt thereof causes an immediate reaction to thereby give rise to a heterogeneous flocculent precipitate, thus deteriorating the usefulness as a thickening agent.

The applicant has proposed, in Japanese Patent Publication No. 41926/1986, a process for preparing a gel usable in a composition of an external preparation by crosslinking a water-soluble polymer of an aliphatic carboxylic acid or a salt thereof with aluminum. Although this process can provide a homogeneous gel, a reaction at a desired rate is difficult, posing such problem that it is difficult to control a change in quality with the lapse of time. Japanese Patent Publication No. 33685/1991 discloses a method wherein crosslinking can be conducted at any desired crosslinking rate. In this method, however, the control system is complicated and an unnecessary metal ion is incorporated, so that the resultant gel is not always satisfactory in the prevention of a change in quality with the lapse of time and irritation to the skin, making it impossible to always prepare a composition of an external preparation having a constant quality.

Skin patch preparations, for example, fomentations for application to the skin, are required to have various characteristics, such as shape retention, water retention, and stability without causing a change in quality with the lapse of time. For this reason, in order to impart or maintain these various characteristics, a polymer gel has been used as a base for fomentations. In the preparation of such fomentations, in order to always provide products having a constant quality free from a change with the lapse of time, when such factors as the working time necessary for processing and the time necessary for coping with a sudden accident are taken into consideration, it is necessary that the viscoelasticity is large enough to permit working persist for 1 to 5 hr, that gelation occurs immediately after the preparation that the-reaction is completed in a short time, and that after being put on the market, the crosslinking continuously proceeds to prevent a change in quality with the lapse of time.

SUMMARY OF THE INVENTION

The present invention has been made under the above circumstances, and an object of the present invention is to gel a water-soluble polymer of an aliphatic carboxylic acid or a salt thereof at a desired reaction rate so as to provide a composition of a skin patch preparation comprising a synthetic polymer gel always having a constant quality and to provide a process for preparing the same.

In view of the above, the present inventors have made various studies with a view to crosslinking a water-soluble polymer of an aliphatic carboxylic acid or a salt thereof with aluminum homogeneously and at a desired crosslinking rate. As a result, they have found that a reaction of a water-soluble polymer of an aliphatic carboxylic acid or a salt thereof with a sparingly soluble aluminum compound, an organic acid containing a hydroxyl group in its molecule as a reaction accelerator, and an ethylenediamine compound and/or citric acid as a reaction inhibitor in the presence of water at pH 4.0 to 6.1 can provide, at any desired reaction rate, a composition of a skin patch preparation comprising a synthetic polymer gel which has excellent various characteristics, is homogeneous and stable, and can always maintain a stable quality, which has lead to the completion of the present invention.

Accordingly, the present invention relates to a composition of a skin patch preparation comprising a synthetic polymer gel prepared by reacting a watersoluble polymer of an aliphatic carboxylic acid or a salt thereof with a sparingly soluble aluminum compound, an organic acid containing a hydroxyl group in its molecule as a reaction accelerator and an ethylenediamine compound and/or citric acid as a reaction inhibitor in the presence of water at pH 4.0 to 6.1, and a process for preparing the same.

The composition of a skin patch preparation comprising a synthetic polymer gel prepared according to the present invention has the following characteristics.

(1) Self-shape retention; Despite the fact that a large amount of water is contained inside the gel, the gel does not have fluidity and has an elasticity high enough to withstand disintegration upon pressing.

(2) Water-holding property; The gel, when compressed with about 90% of water contained therein, does not release water, is slightly humid to the touch on the surface thereof, and does not wet the hand.

(3) Heat stability: The gel, even when put into a hermetically sealed bag of an aluminum foil and placed in a thermostatic chamber at 50° C. for 2 months, can retain its original shape and does not cause oozing of water formed as a result of the phenomenon of syneresis of gel.

(4) Water absorption: Even when the gel contains a large amount of water, additional contact with water results in swelling of the gel to further absorb a large amount of water.

(5) Water release: When the gel is allowed to stand in a room, water is gradually evaporated from the surface thereof. At that time, the latent heat of vaporization is lost, permitting the gel per se to be always kept at a temperature below room temperature.

(6) Stability of quality after the lapse of time: Also after the preparation of a product, crosslinking proceeds and prevents a change in quality with the lapse of time, making it possible to maintain a stable homogeneous quality.

The composition of an external preparation comprising a synthetic polymer gel prepared according to the present invention has the above excellent characteristics and hence can be used for the following various external preparations.

(1) Pharmaceuticals: base of fomentations.

(2) Medical supply: coolants for the affected part at the time of fever.

(3) Cosmetics: pack preparations.

(4) Daily necessities: the composition is properly molded to be used for prevention of sunstroke at the time of extreme heat weather. Alternatively, the composition may be molded into a belt which is wound around the head for cooling purposes.

PREFERRED EMBODIMENTS OF THE INVENTION

Figure 1:
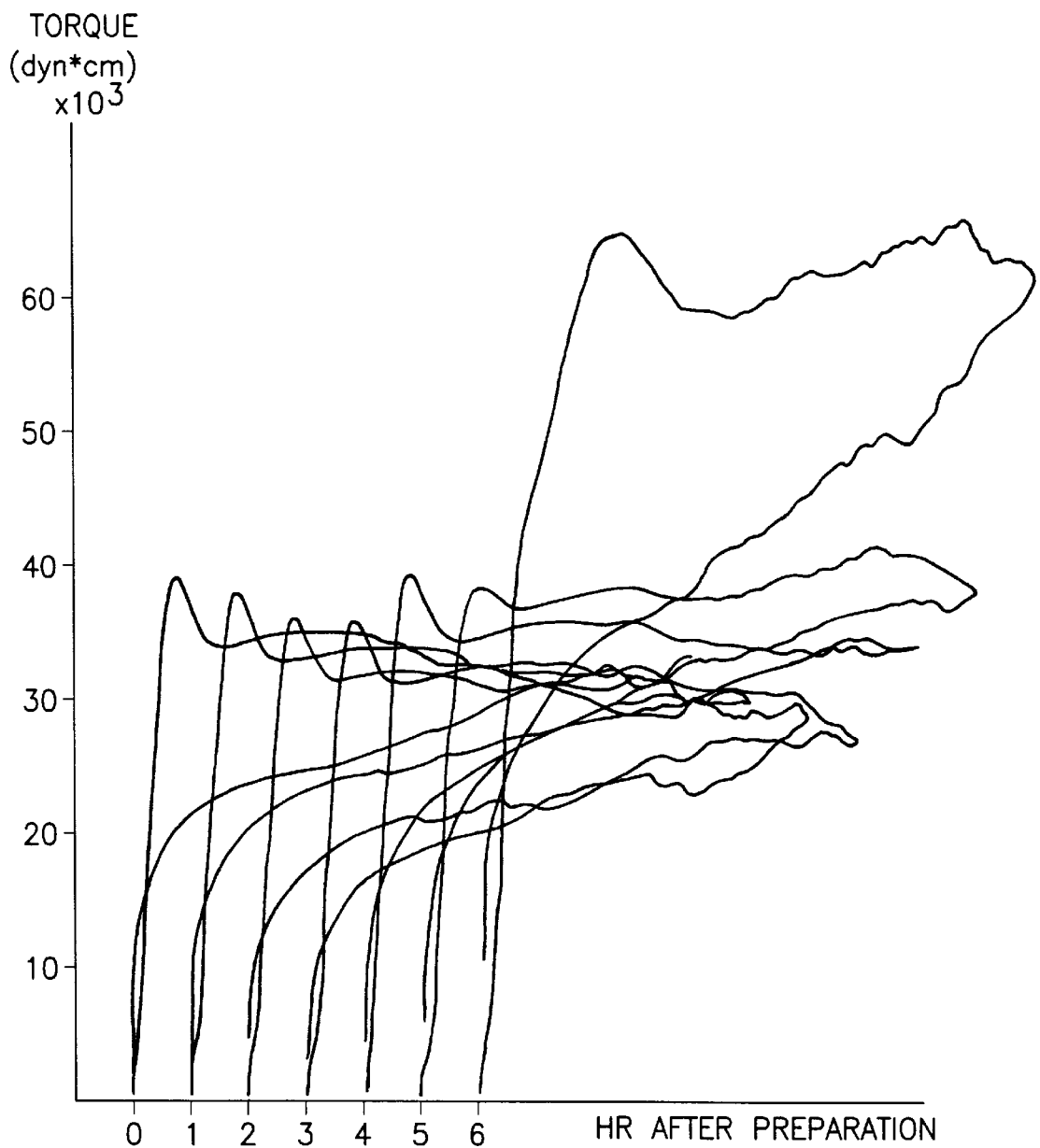
FIG. 1 is a graph showing a change in thixotropic loop of a substrate of a patch for the skin prepared in Example 1 with the lapse of time after the preparation (in the number of revolutions represented in the abscissa, each of the initial points of six chromatograms for the substrate immediately after the preparation and 1 hr, 2 hr, 3 hr, 4 hr, 5 hr, and 6 hr after the preparation is 0 rpm, and the number of revolutions is increased every 1 rpm as shown in FIG. 3)

In the present invention, the water-soluble polymer of an aliphatic carboxylic acid refers to a synthetic polymer compound comprising acrylic acid, methacrylic acid, or maleic anhydride as constituent units, and examples thereof include polyacrylic acid, polymethacrylic acid, and carboxyvinyl polymer. Maleic anhydride is easily hydrolyzed in water to give a carboxylic acid and hence can be regarded as an aliphatic carboxylic acid. These monomers can be classified into those which form homopolymers thereof and those which combine with other monomer(s) to form copolymers. Any of these monomers may be used in the present invention. Examples thereof include a methoxyethylene/maleic anhydride copolymer and a partially neutralized polyacrylic acid.

Although polymers of an aliphatic carboxylic aster, an aliphatic carboxylic acid amide, and an aliphatic nitrile do not fall within the scope of the present invention, products prepared by hydrolyzing a part of these polymers to form free carboxylic acids or salts thereof fall within the scope of the present invention so far as they are soluble in water.

The soluble salt refers to water soluble ones among alkali metal salts, ammonium salts, and salts of primary, secondary, and tertiary organic bases typified by mono-, di-, and triethanolamine salts.

Further, aluminum compounds usable herein include hydroxides, such as aluminum hydroxide, normal salts and basic salts of inorganic and organic acids, such as aluminum chloride, aluminum sulfate, aluminum acetate, and aluminum stearate, aluminum complex salts, and organoaluminum chelate compounds. Even when these aluminum compounds are soluble in water per se, they can be rendered sparingly soluble by suitable treatment. Therefore, the solubility of the aluminum compound per se as the starting compound does not matter.

In order to react the above water-soluble polymer of an aliphatic carboxylic acid or a salt thereof with the aluminum compound to prepare a stable gel, it is preferred that the reaction occur not locally but homogeneously in the whole system. This is because the viscosity of the solution of the water-soluble polymer of a carboxylic acid or a salt thereof is so high that when the aluminum compound solution is added, the reaction proceeds in the interface of both the solutions before homogeneous mixing of both the solutions is attained, resulting in the formation of a flocculent precipitate which is heterogeneous and has poor usefulness unfavorably. According to the present invention, this problem has been solved by using an aluminum compound having low solubility. Even when the aluminum compound has high solubility, it can be converted to a sparingly soluble aluminum hydroxide by dissolving the aluminum compound in water and adding an alkali, such as sodium hydroxide, to the solution to adjust the pH. The sparingly soluble aluminum compound referred to in the present invention thus embraces those which have been rendered sparingly soluble.

Further, in the present invention, when an aluminum compound having high solubility has been dissolved in an oxyacid and then added in a chelate form, the aluminum chelated with the oxyacid is dissociated after homogeneous mixing with an aqueous solution of the water-soluble polymer of an aliphatic carboxylic acid or a salt thereof and transferred into the water-soluble polymer of an aliphatic carboxylic acid or a salt thereof, realizing homogeneous crosslinking.

The rate of the reaction of the above polymer with the aluminum compound is governed by the surface area and solubility of the aluminum compound particles suspended and the pH of the solution. The lower the pH value, the higher the reaction rate. However, when the pH value is excessively low, the gel strength is lowered. On the contrary, when the pH value is around 6, the reaction rate is low. A suitable pH is in the range of from 4.0 to 6.1.

The amount of the aluminum compound added is preferably 0.2 to 15% by weight in terms of aluminum based on the amount of the water-soluble polymer of an aliphatic carboxylic acid or a salt thereof from the viewpoint of preparing a desirable polymer gel.

Addition of an organic acid containing an OH group in its molecule or a salt thereof to the reaction system can increase the reaction rate Organic acids usable herein include those called oxyacids, such as glycolic acid, lactic acid, malic acid, tartaric acid, gluconic acid, and salicylic acid. Among them, tartaric acid is particularly preferred. The reason why the above organic acid functions to promote the above reaction is believed to reside in the chelating capability of the OH group in its molecule, and the OH group and the carboxylic acid are believed to cooperatively act to gradually dissolve the sparingly soluble aluminum salt in the system.

Further, the present invention can be carried out also by adding a sparingly soluble aluminum compound in a solution containing a mixture of two or more polymers of aliphatic carboxylic polymers or salts thereof as described above. For example, a gel prepared by adding an aluminum compound to a solution containing polysodium acrylate in combination with a carboxyvinyl polymer has high elasticity and waterholding capability and hence is very useful as a composition of a skin patch preparation, for example, a base of fomentations. In addition, gelatin, sodium carboxymethylcellulose, sodium alginate and the like, which also can gel using aluminum, may be incorporated.

In the preparation of a composition of a skin patch preparation comprising a synthetic polymer gel, which is significant from the practical viewpoint in the present invention, the amount (w/w %) of the aliphatic carboxylic acid or a salt thereof based on the total amount of the composition is generally 1 to 35%, preferably 2.5 to 25% by weight. When the amount is outside the above range, it is difficult to prepare a gel product which is satisfactory as a composition for a skin patch preparation.

In the present invention, in order to inhibit crosslinking of a water-soluble polymer of an aliphatic carboxylic acid or a salt thereof with aluminum, an ethylenediamine compound and/or citric acid having a higher chelatability with aluminum than the water-soluble polymer of an aliphatic carboxylic acid or a salt thereof is used as a reaction inhibitor. Sodium edetate is particularly preferred as the ethylenediamine compound Since citric acid is an oxyacid, it can act also as a solubilizing agent of the sparingly soluble aluminum compound. Since, however, citric acid has a higher chelatability with aluminum than the water-soluble polymer of an aliphatic carboxylic acid or a salt thereof, it, when used alone, functions as a reaction inhibitor, making it difficult to control the reaction rate unfavorably. For this reason, the use of citric acid in combination with other oxyacid is necessary.

The composition of a skin patch preparation according to the present invention is characterized by comprising a synthetic polymer gel prepared by finally crosslinking the water-soluble polymer of an aliphatic carboxylic acid or a salt thereof with aluminum by utilizing a difference in aluminum chelate forming capability between the materials. For example, a comparison of chelate forming capabilities among a partially neutralized polyacrylic acid, i.e., a water-soluble polymer of an aliphatic carboxylic acid or a salt thereof, tartaric acid and sodium edetate shows that the chelatability is in the order of sodium edetate>partially neutralized polyacrylic acid>tartaric acid. At a pH 4.0 to 6.1, the dispersion of a dry aluminum hydroxide gel in an aqueous solution of a partially neutralized polyacrylic acid and sodium edetate followed by the addition of the tartaric acid to the dispersion causes tartaric acid to act on the dry aluminum hydroxide gel, gradually eluting aluminum. The eluted aluminum is first chelated with sodium edetate, and gels by crosolinking with the partially neutralized polyacrylic acid only when excess aluminum is eluted. That is, gelation does not occur in a period where sodium edetate and aluminum form a chelate, and in this period, a specified viscoelasticity with a fluidity is maintained. Upon the initiation of elution of excess aluminum, the crosslinking with the partially neutralized polyacrylic acid begins, rapidly increasing the viscoelasticity, which results in gelation. That is, the elution rate of aluminum can be regulated by regulating the amount of tartaric acid added, the pH and the reaction temperature, and the time taken for the initiation of gelation can be regulated by regulating the amount of sodium edetate added. Thus, the gelation rate can be freely designed.

In the process according to the present invention, the reaction is completed in a relatively short time. The dissolution of a water-soluble aluminum salt, for example, aluminum sulfate, in an organic acid containing a hydroxyl group in its molecule, for example, an aqueous tartaric acid solution, to form a chelate followed by the addition of the solution develops such a phenomenon that the gel strength is increased about 16 hr after the preparation. This phenomenon can prevent the substrate from being forced out of or passed through the support before the completion of aging due to the application of pressure created by stacking. Thus, the workability can be improved.

Further, the addition of phosphoric acid in an amount of 0.01 to 0.1% by weight based on the total amount of the composition to the reaction system, despite the fact that gelation does not occur during a period necessary for processing, serves to accelerate the gelation rate after the process, shortening the aging period.

The gel prepared according to the process of the present invention can be utilized as a composition of a skin patch preparation for various applications. Therefore, in order to develop delicate properties according to the purposes, if necessary, any suitable additive may be used in the course of the preparation of the composition. Major applications include the use as bases of fomentations and the use in coolants for parts of the body as medical supply or daily necessities. In the field of cosmetics, the use as pack preparations is considered.

In the use of fomentations for cooling of the affected part in a bruise, a sprain and the like, water contained in the composition absorbs heat from the affected part in the form of latent heat of vaporization and hence can be deemed to be an important active ingredient. Further, as described above, when the use of the composition of the present invention as the medical supply or daily necessities only for cooling parts of the body is contemplated, water is an origin of the usefulness. Therefore, in this case, the higher the content of water, the better the effect. In the base of the conventional fomentations, incorporation of a large amount of water lowers the shape retentivity of the base, leading to such inconvenience that the affected part is soiled. By contrast, the composition of a skin patch preparation according to the present invention can contain water in an amount as large as 90% or more by weight, based on the total weight of the composition, which is very useful from the above viewpoint.

EXAMPLES

This invention will now be described in more detail with reference to the following Examples and Comparative Examples.

Example 1

56.5 parts by weight of purified water, 0.1 part by weight of sodium edetate, 2 parts by weight of precipitated silicic acid anhydride (trade name: Aerosil 200), and 0.3 part by weight of titanium oxide were successively put into a mixer with the milling and storage temperature set at 40° C., followed by dissolution and dispersion. One part by weight of a carboxyvinyl polymer (trade name: Carbopol ULT10) was gradually added to the resultant solution, and the mixture was stirred for dissolution 2 for 10 min. A dispersion of 1 part by weight of sodium carboxymethylcellulose (trade name. Daicel 1350) in 4 parts by weight of glycerin was then added, and the mixture was stirred for 10 min for dissolution. The resultant viscous liquid was transferred to a kneader warmed at 40° C. and a solution of 1 part by weight of tartaric acid in 2 parts by weight of purified water was added thereto. The mixture was milled for 5 min, and a dispersion of 0.1 part by weight of dry aluminum hydroxide gel and 6 parts by weight of a partially neutralized polyacrylic acid (trade name: Viscomate NP-700) in 26 parts by weight of glycerin was gradually added thereto. The mixture was milled for 40 min, thereby preparing a substrate of a patch for the skin. The above procedure was repeated to prepare three lots of the substrate.

Example 2

56.45 parts by weight of purified water, 0.1 part by weight of sodium edetate, 2 parts by weight of precipitated silicic acid anhydride (trade name: Aerosil 200), and 0.3 part by weight of titanium oxide were successively put into a mixer with the milling and storage temperature set at 40° C., followed by dissolution and dispersion. One part by weight of a carboxyvinyl polymer (trade name; Carbopol ULT10) was gradually added to the resultant solution, and the mixture was stirred for dissolution for 10 min. A dispersion of 1 part by weight of sodium carboxymethylcellulose (trade name: Daicel 1350) in 4 parts by weight of glycerin was then added, and the mixture was stirred for 10 min for dissolution. The resultant viscous liquid was transferred to a kneader warmed at 40° C. and a solution of 1 part by weight of tartaric acid and 0.05 part by weight of aluminum sulfate in 2 parts by weight of purified water was added thereto. The mixture was milled for 5 min, and a dispersion of 0.1 part by weight of dry aluminum hydroxide gel and 6 parts by weight of a partially neutralized polyacrylic acid (trade name; Viscomate NP-700) in 26 parts by weight of glycerin was gradually added thereto. The mixture was milled for 40 min, thereby preparing a substrate of a patch for the skin, Example 3

56.45 parts by weight of purified water, 0.05 part by weight of phosphoric acid, 0.1 part by weight of sodium edetate, 2 parts by weight of precipitated silicic acid anhydride (trade name: Aerosil 200), and 0.3 part by weight of titanium oxide were successively put into a mixer with the milling and storage temperature set at 40° C., followed by dissolution and dispersion. One part by weight of a carboxyvinyl polymer (trade name: Carbopol ULT10) was gradually added to the resultant solution, and the mixture was stirred for dissolution for 10 min. A dispersion of 1 part by weight of sodium carboxymethyl cellulose (trade name: Daicel 1350) in 4 parts by weight of glycerin was then added, and the mixture was stirred for 10 min for dissolution. The resultant viscous liquid was transferred to a kneader warmed at 40° C. and a solution of 1 part by weight of tartaric acid in 2 parts by weight of purified water was added thereto. The mixture was milled for 5 min, and a dispersion of 0.1 part by weight of dry aluminum hydroxide gel and 6 parts by weight of a partially neutralized polyacrylic acid (trade name: Viscomate NP-700) in 26 parts by weight of glycerin was gradually added thereto. The mixture was milled for 40 min, thereby preparing a substrate of a patch for the skin.

Example 4

56.4 parts by weight of purified water, 0.05 part by weight of phosphoric acid, 0.1 part by weight of sodium edetate, 2 part by weight of precipitated silicic acid anhydride (trade name; Aerosil 200), and 0.3 part by weight of titanium oxide were successively put into a mixer with the milling and storage temperature set at 40° C., followed by dissolution and dispersion. One part by weight of a carboxyvinyl polymer (trade name: Carbopol ULT10) was gradually added to the resultant solution, and the mixture was stirred for dissolution for 10 min. A dispersion of 1 part by weight of sodium carboxymethyl cellulose (trade name: Daicel 1350) in 4 parts by weight of glycerin was then added, and the mixture was stirred for 10 min for dissolution. The resultant viscous liquid was transferred to a kneader warmed at 40° C. and a solution of 1 part by weight of tartaric acid and 0.05 part by weight of aluminum sulfate in 2 parts by weight of purified water was added thereto. The mixture was milled for 5 min, and a dispersion of 0.1 part by weight of dry aluminum hydroxide gel and 6 parts by weight of a partially neutralized polyacrylic acid (trade name: Viscomate NP-700) in 26 parts by weight of glycerin was gradually added thereto. The mixture was milled for 40 min, thereby preparing a substrate of a patch for the skin.

Example 5

56.7 parts by weight of purified water, 2 part by weight of precipitated silicic acid anhydride (trade name: Aerosil 200), and 0.3 part by weight of titanium oxide were successively put into a mixer with the milling and storage temperature set at 40° C., followed by dissolution and dispersion. One part by weight of a carboxyvinyl polymer (trade name: Carbopol ULT10) was gradually added to the resultant solution, and the mixture was stirred for dissolution for 10 min. A dispersion of 1 part by weight of sodium carboxymethylcellulose (trade name: Daicel 1350) in 4 parts by weight of glycerin was then added, and the mixture was stirred for 10 min for dissolution. The resultant viscous liquid was transferred to a kneader warmed at 40° C. and a solution of 0.8 part by weight of tartaric acid and 0.1 part by weight of citric acid in 2 parts by weight of purified water was added thereto. The mixture was milled for 5 min, and a dispersion of 0.1 part by weight of dry aluminum hydroxide gel and 6 parts by weight of a partially neutralized polyacrylic acid (trade name; Viscomate NP-700) in 26 parts by weight of glycerin was gradually added thereto. The mixture was milled for 40 min, thereby preparing a substrate of a patch for the skin.

Example 6

A substrate of a patch for the skin was prepared in the same manner as that of Example 1, except that the amount of the purified water put into the mixer with the milling and storage temperature set at 40° C. was 56.55 parts by weight and the amount of sodium edetate added was 0.05 part by weight.

Example 7

A substrate of a patch for the skin was prepared in the same manner as that of Example 1, except that the amount of the purified water put into the mixer with the milling and storage temperature set at 40° C. was 56.45 parts by weight and the amount of sodium edetate added was 0.15 part by weight.

Example 8

56.5 parts by weight of purified water, 0.1 part by weight of sodium edetate, 2 parts by weight of precipitated silicic acid anhydride (trade name: Aerosil 200), and 0.3 part by weight of titanium oxide were successively put into a mixer with the milling and storage temperature set at 40° C., followed by dissolution and dispersion. One part by weight of a carboxyvinyl polymer (trade name: Carbopol ULT10) was then gradually added to the resultant solution, and the mixture was stirred for dissolution for 10 min. A dispersion of 1 part by weight of sodium carboxymethylcellulose (trade name: Daicel 1350) in 4 parts by weight of glycerin was then added, and the mixture was stirred for 10 min for dissolution. The resultant viscous liquid was transferred to a kneader warmed at 40° C. and a solution of 1 part by weight of tartaric acid in 2 parts by weight of purified water was added thereto. The mixture was milled for 10 min, and a dispersion of 0.1 part by weight of dry aluminum hydroxide gel and 6 parts by weight of a partially neutralized polyacrylic acid (trade name: viscomate NP-700) in 26 parts by weight of glycerin was gradually added thereto. The mixture was milled for 40 min, thereby preparing a substrate of a patch for the skin.

Example 9

A substrate of a patch for the skin was prepared in the same manner as that of Example 1, except that the milling and storage temperature was 35° C.

Example 10

A substrate of a patch for the skin was prepared in the same manner as that of Example 1, except that the milling and storage temperature was 50° C. and the milling time after the addition of the aqueous tartaric acid solution was 10 min.

Comparative Example 1

A substrate of a patch for the skin was prepared in the same manner as that of Example 1, except that 56.6 parts by weight of purified water was added to the mixer with the milling and storage temperature set at 40° C. without adding sodium edetate.

The ingredients and formulations in Examples 1 to 10 and Comparative Example 1 are summarized in Table 1.

TABLE 1

(wt %)

| Ingredients | Ex. 1 | Ex. 2 | Ex. 3 | Ex. 4 | Ex. 5 | Ex. 6 | Ex. 7 | Ex. 8 | Ex. 9 | Ex. 10 | Comp. Ex. 1 |
|---|---|---|---|---|---|---|---|---|---|---|---|
| Partially neutralized polyacrylic acid (Viscomate NP-700) | 6 | 6 | 6 | 6 | 6 | 6 | 6 | 6 | 6 | 6 | 6 |
| Carboxyvinyl polymer (Carbopol ULT10) | 1 | 1 | 1 | 1 | 1 | 1 | 1 | 1 | 1 | 1 | 1 |
| Sodium carboxymetylcellulose (Daicel 1290) | 1 | 1 | 1 | 1 | 1 | 1 | 1 | 1 | 1 | 1 | 1 |
| Precipitated silicic acid anhydride | 2 | 2 | 2 | 2 | 2 | 2 | 2 | 2 | 2 | 2 | 2 |
| Titanium oxide | 0.3 | 0.3 | 0.3 | 0.3 | 0.3 | 0.3 | 0.3 | 0.3 | 0.3 | 0.3 | 0.3 |
| Aluminum hydroxide | 0.1 | 0.1 | 0.1 | 0.1 | 0.1 | 0.1 | 0.1 | 0.1 | 0.1 | 0.1 | 0.1 |
| Tartaric acid | 1 | 1 | 1 | 1 | 0.8 | 1 | 1 | 1 | 1 | 1 | 1 |
| Sodium edetate | 0.1 | 0.1 | 0.1 | 0.1 | 0 | 0.5 | 0.15 | 0.1 | 0.1 | 0.1 | 0 |
| Citric acid | 0 | 0 | 0 | 0 | 0.1 | 0 | 0 | 0 | 0 | 0 | 0 |
| Aluminum sulfate | 0 | 0.05 | 0 | 0.05 | 0 | 0 | 0 | 0 | 0 | 0 | 0 |
| Phosphoric acid | 0 | 0 | 0.05 | 0.05 | 0 | 0 | 0 | 0 | 0 | 0 | 0 |
| Glycerin | 30 | 30 | 30 | 30 | 30 | 30 | 30 | 30 | 30 | 30 | 30 |
| Purified water | 58.5 | 58.45 | 58.45 | 58.4 | 58.7 | 58.55 | 58.45 | 58.5 | 58.5 | 58.5 | 58.6 |
| Total | 100 | 100 | 100 | 100 | 100 | 100 | 100 | 100 | 100 | 100 | 100 |
| Preparation and storage temp. | 40° | 40° | 40° | 40° | 40° | 40° | 40° | 40° | 35° | 50° | 40° |

For each substrate prepared in Examples 1 to 10 and comparative Example 1, a part of the substrate was spread on a nonwoven fabric of polypropylene in a thickness of 1 mm, covered with a polypropylene film, and stored in an aluminum laminate bag to prepare samples for evaluation of aging period. The remnaining substrates were stored as samples for evaluation of gel strength in a kneader.

[Evaluation]

Figure 2:
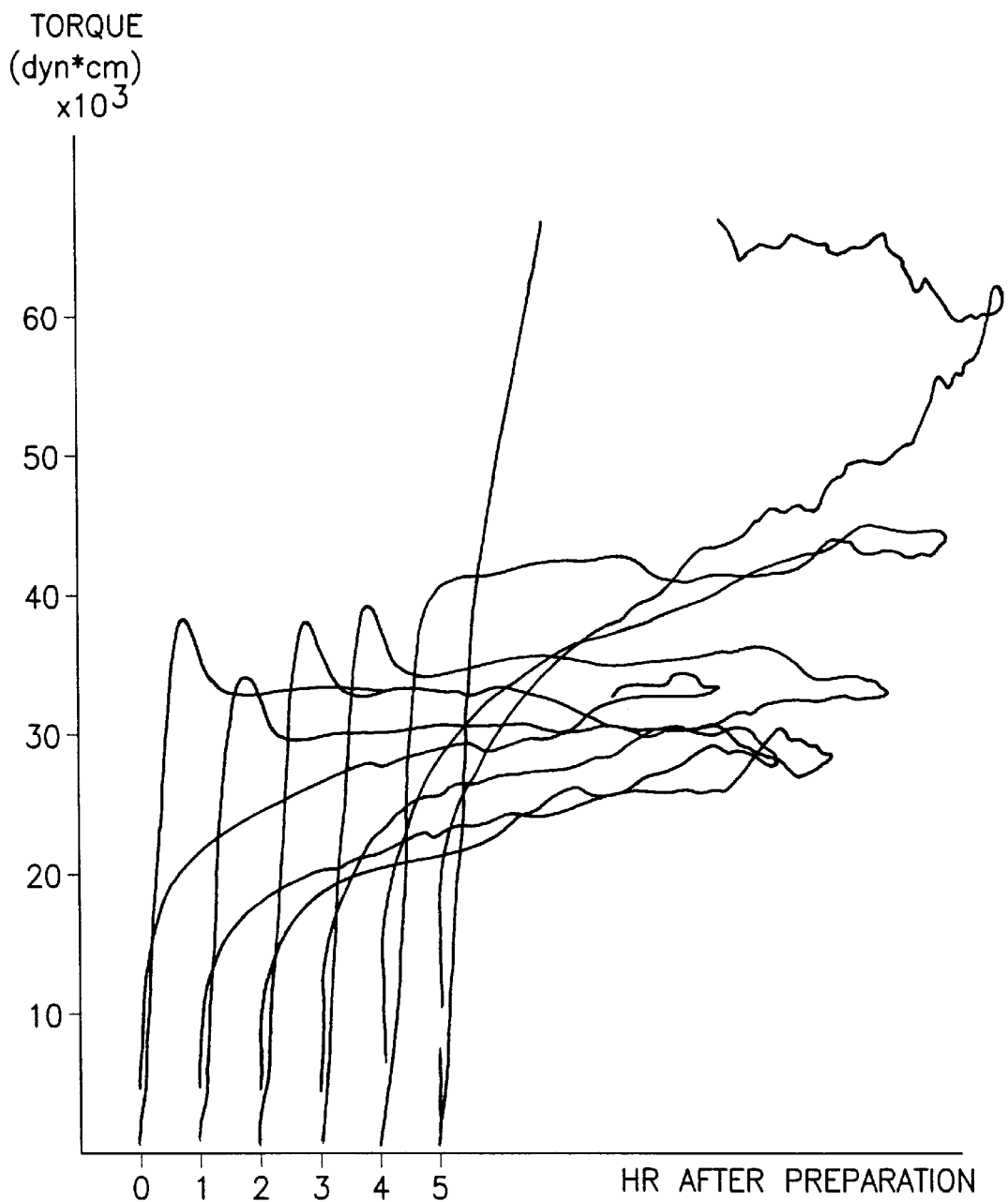
FIG. 2 is a graph showing a change in thixotropic loop of a substrate of a patch for the skin prepared in Example 2 with the lapse of time after the preparation (in the number of revolutions represented in the abscissa, each of the initial points of six chromatograms for the substrate immediately after the preparation and 1 hr. 2 hr. 3 hr, 4 hr, and 5 hr after the preparation is 0 rpm, and the number of revolutions is increased every 1 rpm as shown in FIG. 3)
Figure 3:
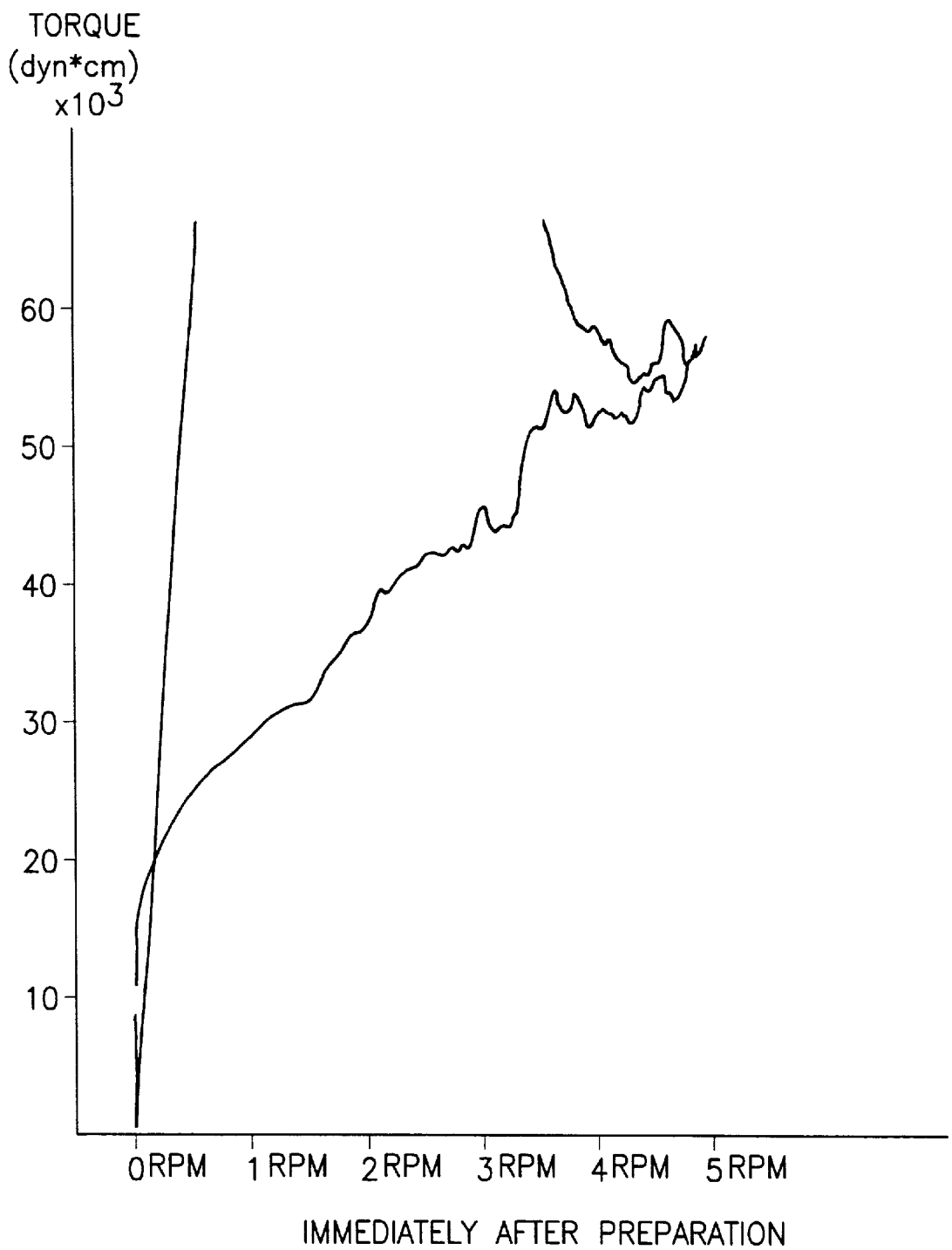
FIG. 3 is a graph showing a change in thixotropic loop of a substrate of a patch for the skin prepared in comparative Example 1 with the lapse of time after the preparation.

For each sample for evaluation of gel strength, the gel strength was measured with a cone plate type viscometer imnmediately after the preparation and during storage at the preparation temperature. In this case, during the storage, the gel strength was measured every one hr. At that time, the gel strength was read from the thixotropic loop to confirm the reaction rate. At the same time, the hardness of the substrate was evaluated in a sensory manner in terms of the time taken for the gelation to proceed to such an extent that the fluidity is lost making it impossible to spread the substrate onto the nonwoven fabric. Further, for each sample for evaluation of aging period, 16 hr after the completion of the preparation, five pieces each having a size of 1 cm×1 cm for each sample were shaken in 50 ml of purified water at 37° C., and the light transmittance (400 nm) of the supernatant was measured. In this case, the aging period was evaluated by taking the time necessary for the light transmittance to reach 90% or more as a standard. The results of each evaluation are summarized in Table 2, and a part of the thixotropic loops is shown in FIGS. 1, 2 and 3. In FIGS. 1 to 3, the ordinate represents the value (dyne×cm) provided by measurement with a torque meter, and the abscissa represents the number of revolutions.

TABLE 2

| Classification of sample | Spread-permitting time | Light transmittance (%) | | | | Aging period (day) |
| --- | --- | --- | --- | --- | --- | --- |
| | | Next day | 2nd day | 3rd day | 4th day | |
| Ex. 1-1 | 5 hr | 80.6 | 93.7 | 97.3 | 99.3 | 2 |
| Ex. 1-2 | 5 hr | 88.5 | 94.5 | 97.3 | 99.7 | 2 |
| Ex. 1-3 | 5 hr | 83.4 | 92.5 | 98.5 | 98.8 | 2 |
| Ex. 2 | 4 hr | 91.0 | 94.5 | 97.5 | 99.2 | 1 |
| Ex. 3 | 4 hr | 92.1 | 95.4 | 97.5 | 99.5 | 1 |
| Ex. 4 | 3.5 hr | 91.5 | 93.4 | 98.0 | 98.5 | 1 |
| Ex. 5 | 6 hr | 70.5 | 82.5 | 94.5 | 98.0 | 3 |
| Ex. 6 | 2 hr | 93.5 | 99.5 | 98.1 | 99.3 | 1 |
| Ex. 7 | 7 hr | 44.5 | 56.4 | 86.5 | 92.5 | 4 |
| Ex. 8 | 1 hr | 92.5 | 99.0 | 98.5 | 98.5 | 1 |
| Ex. 9 | 6 hr | 75.8 | 88.1 | 91.6 | 93.1 | 3 |
| Ex. 10 | 1 hr | 96.5 | 99.8 | 97.5 | 98.5 | 1 |
| Comp. Ex. | 0 hr | 99.5 | 99.4 | 98.2 | 99.0 | 0 |

* When the light transmittance exceeded 90%, it was judged that the sample was fully aged.

The comparison of Comparative Example 1 wherein no sodium edetate was incorporated with Example 6 wherein 0.05 part by weight of sodium edetate was incorporated, Example 1 wherein 0.1 part by weight of sodium edetate was incorporated, and Example 7 wherein 0.15 part by weight of sodium edetate was incorporated shows that increasing the amount of sodium edetate added resulted in increased spread-permitting time and increased aging time. When sodium edetate was added, the viscoelasticity remained substantially unchanged and thereafter the gelation rapidly proceeded resulting in hardening. Therefore, sodium edetate is likely to form a chelate with aluminum more easily than a partially neutralized polyacrylic acid, so that the time taken for aluminum to crosslink with the partially neutralized polyacrylic acid can be designed by regulating the amount of sodium edetate added.

The comparison of Example 9 wherein the preparation and storage time was 35° C. with Example 1 wherein the preparation and storage time was 40° C. and Example 10 wherein the preparation and storage time was 50° C. shows that the spread-permitting time was shortened with the temperature rise.

Further, the comparison of Example 1 wherein the period of time between the completion of the addition of tartaric acid and the initiation of the addition of the partially neutralized polyacrylic acid is 5 min with Example 8 wherein the above time is 10 min shows that the spread-permitting time was shortened as the above time was lengthened.

From the above facts, it has been confirmed that the time taken for aluminum to be eluted from the dry aluminum hydroxide aluminum gel can be designed by regulating the milling temperature and the period of time between the completion of the addition of tartaric acid and the initiation of the addition of the partially neutralized polyacrylic acid.

The comparison of Examples 2 to 4 with Example 1 shows that the addition of aluminum sulfate or phosphoric acid resulted in the shortened period of time for aging.

As with the addition of sodium edetate, the addition of citric acid in Example 5 resulted in the delayed gelation initiation time.

The preparation of three lots in Example 1 demonstrated reproducible reactivity.

Further, the above sample for evaluation of aging period, prepared by spreading the substrate of Example 1 on non-woven fabric of polypropylene, was cut into a size of 5 cm and 12 cm and applied to the forehead to evaluate the feel of use. As a result, the tack strength persisted for a long period of time and the feel of use was excellent. Further, the same sample was applied to the skin of a rabbit to conduct a test on primary irritation to the skin and a test on accumulated irritation to the skin for 28 days. As a result, in these tests, no irritation to the skin was observed. Further, the same sample was stored at 50° C. for two months in order to evaluate the stability. As a result, it was found to be stable without causing disintegration of the gel and separation of the liquid component.

As is apparent from the foregoing description, in a homogeneous dispersion of a sparingly soluble aluminum compound in a water-soluble polymer of an aliphatic carboxylic acid or a salt thereof followed by the action of an oxyacid, the elution rate of aluminum can be regulated by regulating the milling temperature and time. Further, since the ethylenediamine compound and/or citric acid preferentially forms a chelate with aluminum to inhibit gelation, the regulation of the amounts of these compounds added enables the regulation of the gelation initiation time. Therefore, the above regulation serves to design a desired gelation rate and, at the same time, to completely control the crosslinking reaction, thus facilitating the process control. Thus, it is possible to provide a composition of a skin patch preparation, which is excellent in various characteristics as the composition of a skin patch preparation, has a constant quality, does not change with the lapse of time, and is very safe and useful, and a process for preparing the same. Therefore, drawbacks found in the conventional products, including that, due to the face that the crosslinking reaction cannot be regulated, the composition is soft and sticky during a short period of time after the preparation despite the same preparation and becomes hard and causes a lowering in tack strength after the lapse of a long period of time. Further, unlike the conventional products, the composition of the present invention serves to eliminate the need to be stored in a storehouse until the degree of crosslinking becomes constant.

What is claimed is:

1. A composition for a skin patch preparation comprising a synthetic water holding polymer gel prepared by reacting, in the presence of water and at a pH of 4.0 to 6.1, a water-aoluble polymer of an aliphatic carboxylic acid or a salt thereof in an amount of 1 to 30% by weight based on the total weight of the composition, with a sparingly soluble aluminum compound in an amount of 0.2 to 15% by weight in terms of aluminum based on the weight of said water-soluble polymer, a reaction accelerator consisting essentially of an organic acid containing a hydroxyl group in its molecule, said organic acid being selected from the group consisting of glycolic acid, lactic acid, malic acid, tartaric acid, gluconic acid and salicylic acid, said organic acid being present in an amount effective to increase the reaction rate of said water-soluble polymer and said aluminum compound, and a reaction inhibitor consisting essentially of an ethylenediamine compound, said ethylenediamine compound being present in an amount effective for control of the rate of initiation of gelation.

2. A process for preparing a composition for a skin patch preparation comprising a synthetic water holding polymer gel, which comprises reacting, in the presence of water and at a pH of 4.0 to 6.1, a water-soluble polymer of an aliphatic carboxylic acid or a salt thereof in an amount of 1 to 30% by weight based on the total weight of the composition with a sparingly soluble aluminum compound in an amount of 0.2 to 15% by weight in terms of aluminum based on the weight of said water-soluble polymer, a reaction accelerator consisting essentially of an organic acid containing a hydroxyl group in its molecule, said organic acid being selected from the group consisting of glycolic acid, lactic acid, malic acid, tartaric acid, gluconic acid and salicylic acid, said organic acid being present in an amount effective to increase the reaction rate of said water-soluble polymer and said aluminum compound, and a reaction inhibitor consisting essentially of an ethylenediamine compound, said ethylenediamine compound being present in an amount effective for control of the rate of initiation of gelation.

3. The process for preparing a composition according to claim 2, wherein the aluminum salt is added as a solution thereof in the organic acid containing a hydroxyl group in its molecule.

4. The process for preparing a composition according to claim 2, which further comprises adding phosphoric acid.

5. The process for preparirig a composition of an external preparation Comprising a synthetic polymer gel according to claim 3, wherein phosphoric acid is added.

6. The composition according to claim 1, wherein the water-soluble polymer of an aliphatic carboxylic acid is a synthetic polymer compound comprising acrylic acid, methacrylic acid or maleic anhydride.

7. The composition according to claim 1, wherein the water-soluble polymer of an aliphatic carboxylic acid is selected from the group consisting of polyacrylic acid, polymethacrylic acid, carboxyvinyl polymer and a methoxyethylene/maleic anhydride copolymer.

8. The composition according to claim 7, wherein the aluminum compound is selected from the group consisting of aluminum hydroxide, aluminum chloride, aluminum sulfate, aluminum acetate and aluminum stearate.

9. The composition according to claim 8, wherein the organic acid is tartaric acid and the ethylenediamine compound is sodium edetate.

10. The composition according to claim 8, which further comprises 0.01 to 0.1% by weight of phosphoric acid based on the total amount of the composition.

11. The process according to claim 2, wherein the water-soluble polymer of an aliphatic carboxylic acid is a synthetic polymer compound comprising acrylic acid, methacrylic acid or maleic anhydride.

12. The process according to claim 11, wherein the water-soluble polymer of an aliphatic carboxylic acid is selected from the group consisting of polyacrylic acid, polymethacrylic acid, carboxyvinyl polymer and a methoxyethylene/maleic anhydride copolymer.

13. The process according to claim 12, wherein the aluminum compound is selected from the group consisting of aluminum hydroxide, aluminum chloride, aluminum sulfate, aluminum acetate and aluminum stearate.

14. The process according to claim 13, wherein the organic acid is tartaric acid and the ethylenediamine compound is sodium edetate.

15. The process according to claim 13, which further comprises adding 0.01 to 01% by weight of phosphoric acid based on the total amount of the composition.

* * * * *